United States Patent [19]

Knifton

[11] 4,357,477

[45] Nov. 2, 1982

[54] PROCESS FOR PREPARING ETHYLENE GLYCOL MONOALKYL ETHERS

[75] Inventor: John F. Knifton, Austin, Tex.

[73] Assignee: Texaco Inc., White Plains, N.Y.

[21] Appl. No.: 316,192

[22] Filed: Oct. 29, 1981

[51] Int. Cl.³ .............................................. C07C 41/01
[52] U.S. Cl. .................................... 568/678; 568/672; 252/431 C; 252/431 A
[58] Field of Search .............................. 568/678, 672

[56] References Cited

U.S. PATENT DOCUMENTS 2,429,878 10/1947 Gresham et al. ................... 568/678
4,062,898 12/1977 Dubeck et al. ...................... 568/678

Primary Examiner—Howard T. Mars
Attorney, Agent, or Firm—Carl G. Ries; Jack H. Park; Walter D. Hunter

[57] ABSTRACT

This invention pertains to the production of ethylene glycol monoalkyl ethers by reaction of carbon monoxide and hydrogen with (a) formaldehyde and an alcohol or (b) an acetal in the presence of a catalyst comprising a cobalt-containing compound and a tin or germanium promoter.

24 Claims, No Drawings

PROCESS FOR PREPARING ETHYLENE GLYCOL MONOALKYL ETHERS

BACKGROUND OF THE INVENTION

1. Field of the Invention

This invention relates to a process for the preparation of ethylene glycol monoalkyl ethers by the reaction of synthesis gas with (a) formaldehyde and an alcohol or (b) an acetal using a specific catalyst system.

2. Prior Art

There is a ever increasing need for a wide variety of glycol monoalkyl ethers of differing carbon numbers and structures which have become important present articles of commerce. Such ethers are employed in a wide variety of applications as solvents, reaction media, etc. In conventional processes an olefin oxide such as ethylene oxide is first prepared from an olefin and reacted with a suitable alcohol to give the desired glycol alkyl ether. Since the cost of materials derived from petroleum sources has been rising rapidly, research efforst are now being made to find new processes for producing these glycol ethers which do not utilize an olefin as a starting material. One of the newer methods for the preparation of glycol monoalkylethers, in which an acetal is reacted with carbon monoxide and hydrogen in the presence of a cobalt carbonyl catalyst, is described in German Pat. Nos. 875,802 and 890,945. This process suffers from several disadvantages including a low selectivity of the glycol ether and decomposition of the carbonyl catalyst during recovery of the product from the reaction mixture.

In U.S. Pat. No. 4,071,568 a process for making glycol monoalkyl ethers is disclosed in which the catalyst utilized is cobalt carbonyl combined with a trivalent organic phosphorus compound such as tri-n-butylphosphine which is reported to give better selectivity. Other process for preparing glycol monoalkyl ethers are described in U.S. Pat. No. 4,062,898 and in German Pat. No. 2,741,589.

One of the objects of this invention is to provide a novel process for preparing ethylene glycol monoalkyl ethers by means of a unique catalyst system in which the feedstock utilized comprises synthesis gas and (1) formaldehyde and an alcohol or (2) an acetal.

Another object of this invention is to provide a process for producing ethylene glycol alkyl ethers in high yield.

SUMMARY OF THE INVENTION

In this invention glycol monoalkyl ethers are prepared by reaction of synthesis gas with (1) formaldehyde and an alcohol, or (2) an acetal, in the presence of a catalyst comprising a cobalt-containing compound and at least one tin - or germanium-containing promoter.

One embodiment of the process of this invention is shown in the following equation where for purposes of illustration the reaction of carbon monoxide, hydrogen, formaldehyde and an alcohol is shown:

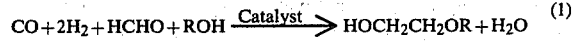
(1)

When an acetal, hydrogen and carbon monoxide are reacted according to the process of this invention the reaction is as follows:

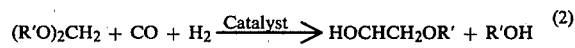
(2)

A wide variety of alcohols and acetals may be employed in the process of this invention.

Substantial yields of the ethylene glycol monoalkyl ethers are achieved with this novel process. Advantageously, the process is conducted under moderate conditions of temperature and pressure.

DETAILED DESCRIPTION OF THE INVENTION

This invention relates to a process for preparing ethylene glycol monoalkyl ethers which comprises reacting hydrogen, carbon monoxide, and a material selected from the group consisting of:

(a) formaldehyde and an alcohol of the formula

ROH wherein R is alkyl of from 1 to 10 carbon atoms and
(b) an acetal of the formula:

$(R'O)_2CH_2$, wherein R' is alkyl of from 1 to 10 carbon atoms, in the presence of a catalyst comprising a cobalt-containing compound and a promoter selected from the group consisting of a tin-containing compound and a germanium-containing compound at superatmospheric pressures of about 500 psi or greater and at a temperature of about 50° to about 300° C. until substantial formation of the said ethylene glycol monoalkyl ethers has been achieved and recovering the said ethers from the reaction mixture.

In carrying out the reaction of this invention selectively to produce high yields of the desired ethylene glycol monoalkylethers it is necessary to supply sufficient carbon monoxide, hydrogen, and (a) formaldehyde and an alcohol or (b) an acetal to at least satisfy the stoichiometry of equations (1) or (2) above although an excess of one or more of the reactants over the stoichiometric amounts may be present. Optionally, when an acetal is reacted with hydrogen and carbon monoxide according to equation (2) above the reaction may be conducted, if desired, in the presence of an alcohol of the formula:

R"OH, wherein R" is alkyl of from 1 to 10 carbon atoms.

Catalysts that are suitable for use in the practice of this invention contain cobalt. The cobalt-containing compounds may be chosen from a wide variety of organic or inorganic compounds, complexes, etc., as will be shown and illustrated below. It is only necessary that the catalyst precursor actually employed contain said metal in any of its ionic states. The actual catalytically active species is then believed to comprise cobalt in complex combination with carbon monoxide and hydrogen. The most effective catalyst is achieved where the cobalt hydrocarbonyl type species are solubilized in the alcohol or acetal co-reactant.

The cobalt-containing catalyst precursors may take many different forms. For instance, the cobalt may be added to the reaction mixture in an oxide form, as in the case of, for example, cobalt(II) oxide (CoO) or cobalt- (II, III) oxide (Co$_3$O$_4$). Alternatively, it may be added as the salt of a mineral acid, as in the case of cobalt(II) chloride (CoCl$_2$), cobalt(II) chloride hydrate (CoCl$_2$O.6H$_2$O), cobalt(II) bromide (CoBr$_2$), cobalt(II) iodide (CoI$_2$) and cobalt(II) nitrate hydrate (Co(NO$_3$)$_2$.6H$_2$O), etc., or as the salt of a suitable organic carboxylic acid, for example, cobalt(II) formate, cobalt(II) acetate, cobalt(II) proprionate, cobalt naphthenate, cobalt acetylacetonate, etc. The cobalt may also be added to the reaction zone as a carbonyl or hydrocarbonyl derivative. Here, suitable examples include dicobalt octacarbonyl, (Co$_2$(CO)$_8$), cobalt hydrocarbonyl, (HCo(CO)$_4$) and substituted carbonyl species such as the triphenylphosphine cobalt tricarbonyl dimer, etc., Preferred cobalt-containing compounds include oxides of cobalt, cobalt salts of a mineral acid, cobalt salts of organic carboxylic acids and cobalt carbonyl or hydrocarbonyl derivatives. Among these, particularly preferred are cobalt(II) chloride, cobalt acetylacetonate, cobalt(II) acetate, cobalt(II) propionate, and dicobalt octacarbonyl.

In the process of this invention the reaction is conducted in the presence of a catalyst comprising a cobalt-containing compound and a tin - or germanium-containing promoter. The cobalt-containing compound employed may be a cobalt carbonyl or a compound capable of forming a cobalt carbonyl under reaction conditions. Usually, the cobalt-containing compound and the promoter are separately introduced into the reaction system where the complex is formed with the cobalt-containing compound under reaction conditions.

The tin-containing promoter compounds which may be utilized with the cobalt-containing compounds in this process may also take many different forms. For instance, the tin may be added to the reaction mixture in elemental form, or in the form of a halide, such as stannic chloride, stannous iodide, stannic bromide, or a hydrocarbyl tin compound such as tetraphenyltin, tetra-n-butyltin, hexamethylditin, tetramethyltin and dibutyl diphenyltin, or an organo-halide tin compound such as trimethyltin chloride, di-t-butyltin dichloride, dimethyltin dichloride, methyltin trichloride, phenyltin trichloride, triethyltin bromide, trimethyltin bromide and tributyltin bromide, or an organotin hydride such as tributyltin hydride, or an organotin oxide such as dimethyltin oxide and diphenyltin oxide, or a carboxylate such as tin(II) caproate, tributyltin acetate and tri-n-propyltin acetate, or an oxide such as stannous oxide and stannic oxide.

The preferred tin-containing promoter compounds are the organo-halide tin compounds. Among these, particularly preferred are trimethyltin chloride, tributyltin chloride and tributyltin bromide.

The germanium-containing promoter compounds which may be utilized with the cobalt-containing compounds in this process may also take many different forms. For instance, the germanium may be added to the reaction mixture in the form of a halide, such as germanium tetrachloride, germanium diiodide and germanium tetrabromide, or as a hydrocarbylgermanium compound such as tetra-n-butylgermanium, tetraethylgermanium, tetraphenylgermane and tetramethylgermane, or an organohalide germanium compound such as diphenylgermanium chloride, methylgermanium trichloride, phenylgermanium trichloride, tri-n-butylgermanium iodide, triethylgermanium chloride, triethylgermanium iodide, trimethylgermanium chloride, triphenylgermanium bromide and triphenylgermanium chloride or an organogermanium hydride, such as triphenylgermanium hydride, or an organogermanium oxide or carboxylate such as triphenylgermanium acetate, or a germanium alkoxide such as germanium butoxide, germanium ethoxide and germanium methoxide.

The preferred germanium-containing promoter compounds are the organo-halide germanium compounds the hydrocarbylgermanium compounds and the organogermanium hydridges. Among these, particularly preferred are triphenylgermanium bromide, triphenylgermanium hydride, trimethylgermanium chloride, triphenylgermanium chloride, trimethylgermanium bromide, triethylgermanium chloride, tetraphenylgermane and tetraethygermane.

The number of gram moles of the tin - or germanium-containing compound employed per gram atom of cobalt can be varied widely and is generally in the range of 0.01 to 100 and preferably from 0.1 to 5.

Alcohols suitable as co-reactants with formaldehyde and synthesis gas in the process of this invention have the formula:

ROH where R is alkyl of from 1 to 10 carbon atoms. Suitable alcohols include methanol, ethanol, propanol, butanol, heptanol, decanol, etc. and isomers thereof.

In addition to formaldehyde, compounds capable of releasing formaldehyde under reaction conditions such as aldehyde polymers including paraformaldehyde and trioxane may be utilized in the process of this invention.

Acetals which may be utilized in the process of this invention include compounds of formula:

(R'O)$_2$CH$_2$, where R' is alkyl of from 1 to 10 carbon atoms as exemplified by methyl, ethyl, butyl, hexyl, nonyl, etc. and isomers thereof. The preferred acetals include dimethoxymethane, di-n-butoxymethane, diethoxymethane, and dipropoxymethane.

The quantity of cobalt catalyst employed in the instant invention is not critical and may vary over a wide range. In general, the novel process is desirably conducted in the presence of a catalytically effective quantity of one or more of the active cobalt species together with one or more of the tin - or germanium-containing promoters which gives the desired products in reasonable yields. The reaction proceeds when employing as little as about $1 \times 10^{-6}$ weight percent and even lesser amounts of cobalt, basis the total weight of the reaction mixture. The upper concentration is dictated by a variety of factors including catalyst cost, partial pressures of carbon monoxide and hydrogen, operating temperature, etc. A cobalt catalyst concentration of from about $1 \times 10^{-5}$ to about 10 weight percent cobalt, based on the total weight of reaction mixture, is generally desirable in the practice of this invention.

The temperature range which can usefully be employed in these syntheses is a variable dependent upon other experimental factors, including the choice of the alcohol employed with formaldehyde or the particular acetal, the pressure, and the concentration and choice of particular species of the cobalt-containing compound and the tin - or germanium-containing promoter among other things. The range of operability is from about 50° to about 300° C. when superatmospheric pressures of syngas are employed. A narrower range of about 100° to about 250° C. represents the preferred temperature range.

Superatmospheric pressures of about 500 psi or greater lead to substantial yields of desirable ethylene glycol ethers by the process of this invention. A preferred operating range is from about 1000 psi to about 5000 psi, although pressures above 5000 psi also provide useful yields of the desired acid. The pressures referred to here represent the total pressure generated by all the reactants, although they are substantially due to the carbon monoxide and hydrogen fractions in these examples.

The relative amounts of carbon monoxide and hydrogen which may be initially present in the syngas mixture are variable, and these amounts may be varied over a wide range. In general, the mole ratio of $CO:H_2$ is in the range from about 20:1 up to about 1:20, preferably from about 5:1 to 1:5, although ratios outside these ranges may also be employed. Particularly in continuous operations, but also in batch experiments, the carbon monoxide-hydrogen gaseous mixtures may also be used in conjunction with up to 50% by volume of one or more other gases. These other gases may include one or more inert gases such as nitrogen, argon, neon and the like, or they may include gases that may, or may not, undergo reaction under CO hydrogenation conditions, such as carbon dioxide, hydrocarbons such as methane, ethane, propane and the like, ethers such as dimethyl ether, methylethyl ether and diethyl ether.

As far as can be determined, without limiting the invention thereby, the one-step process disclosed herein leads primarily to the formation of ethylene glycol monoalkyl ether products. Ethylene glycol dialkyl ether products are also formed, and in the case, for example, where formaldehyde and n-butanol are the co-reactants, the principal products are ethylene glycol monobutyl ether and ethylene glycol dibutyl ether. Diethylene glycol monobutyl ether, methanol, butyl formate and water are also detected in the liquid product fraction.

The novel process of this invention can be conducted in a batch, semi-continuous or continuous fashion. The catalyst may be initially introduced into the reaction zone batchwise, or it may be continuously or intermittently introduced into such a zone during the course of the synthesis reaction. Operating conditions can be adjusted to optimize the formation of the desired ether product, and said material may be recovered by methods well known in the art, such as distillation, fractionation, extraction and the like. A fraction rich in cobalt and tin or germanium catalyst components may then be recycled to the reaction zone, if desired, and additional products generated.

The products have been identified in this work by one or more of the following analytical procedures, viz, gas-liquid phase chromatography (glc), infrared (ir), mass spectrometry, nuclear magnetic resonance (nmr) and elemental analyses, or a combination of these techniques. Analyses have, for the most part, been by parts in weight; all temperatures are in degrees centigrade and all pressures in pounds per square inch gauge (psig).

The following examples which illustrate various embodiments of the invention are to be considered not limitative.

EXAMPLE I

To a 450 ml glass-lined, pressure reactor was charged a mixture of dicobalt octacarbonyl (2 mmole Co), triphenylgermanium bromide (2 mmole) and paraformaldehyde (0.1 mole) in 37.1 g of n-butanol (0.5 mole). The mixture was flushed with nitrogen, the reactor sealed, flushed with $CO/H_2$ (1:1 molar ratio), pressured to 2700 psig with 2:1 molar ratio syngas ($H_2/CO$) and then heated to 160° C. with agitation. After four hours, the reactor was allowed to cool, the gas pressure (2500 psig) noted, the excess gas sampled and vented, and the deep red liquid product (44.5 g) recovered.

Analysis (glc and Karl Fischer titration) of the liquid product showed it to contain:

12.2 wt. % ethylene glycol monobutyl ether
1.4 wt. % ethylene glycol dibutyl ether
1.2 wt. % water
71.4 wt. % unreacted n-butanol.

Estimated yield of ethylene glycol monobutyl ether (basis formaldehyde charged) was 46 mole percent. Total glycol monobutyl plus dibutyl ether yield was 50 mole percent.

Analysis of the liquid product by atomic adsorption showed it to contain >98% of the cobalt originally charged. There was no solid product phase.

Typical off-gas samples showed the presence of:

58% hydrogen
37% carbon monoxide
3.5% carbon dioxide.

The glycol monobutyl ethers were recovered from the crude liquid product by fractional distillation in vacuo.

EXAMPLE 2

To a 450 ml glass-lined pressure reactor was charged a mixture of dicobalt octacarbonyl (2 mmole Co), triphenylgermanium bromide (2.0 mmoles), dibutoxymethane (0.1 mole) in 22.2 g of n-butanol (0.3 mole). The mixture was flushed with nitrogen, the reactor sealed, flushed with $CO/H_2$ (1:2 molar), was pressured to 2700 psig with 1:2 molar syngas ($CO/H_2$) and then heated to 160° C. with agitation. After four hours, the reactor was allowed to cool, the gas pressure (2300 psig) noted, the excess gas sampled and vented, and the deep reddish-brown liquid product (43.0 g) recovered.

Analysis (glc and Karl Fisher titration) of the liquid product showed it to contain:

11.6 wt. % ethylene glycol monobutyl ether
3.5 wt. % ethylene glycol dibutyl ether
1.7 wt. % water
69.2 wt. % butanol.

Estimated yield of ethylene glycol monobutyl ether (basis dibutoxymethane charged) was 41 mole percent. Total glycol monobutyl plus dibutyl ether yield was 50 mole percent.

Analysis of the liquid product by atomic adsorption showed it to contain 97% of the cobalt originally charged. There was no solid product phase.

Typical off-gas samples showed the presence of:

58% hydrogen
34% carbon monoxide 1.9% carbon dioxide.

EXAMPLE 3

Following the procedure of Examples 1 and 2, the reactor was charged with a mixture of dicobalt octacarbonyl (2 mmole Co), triphenylgermanium bromide (2 mmole), dimethoxymethane (0.1 mole) in 9.6 g of methanol (0.3 mole). The mixture was flushed with nitrogen, the reactor sealed, flushed with $CO/H_2$ (1:2 molar), pressured to 2700 psig with 1:2 molar syngas ($CO/H_2$) and then heated with agitation to 200° C. After four hours, the reactor was allowed to cool, the gas pressure (2450 psig) noted, the excess gas sampled and vented, and the black liquid product (18.3 g) recovered.

Analysis of the liquid product showed it to contain:

9.8 wt. % ethylene glycol monomethyl ether
3.2 wt. % ethylene glycol dimethyl ether
8.9 wt. % water
9.1 wt. % dimethoxymethane
60.5 wt. % methanol.

Typical off-gas samples showed the presence of:

54% hydrogen
32% carbon monoxide
1.1% carbon dioxide
0.5% methane.

EXAMPLE 4–18

A number of additional examples were carried out using the procedure of Example I in which a variety of tin - and germanium-containing promoters were employed along with cobalt octacarbonyl catalyst. Data relating to these examples are shown in Tables 1 and 2 which follows. Specifically:

(a) Examples 4 to 9 illustrate the effectiveness of dicobalt octacarbonyl coupled with various germanium promoters, including triphenylgermanium hydride, tetraphenylgermane, tetraethylgermane, triphenylgermanium chloride, trimethylgermanium bromide and triethylgermanium chloride.

(b) Examples 10 to 18 demonstrate the effective use of dicobalt octacarbonyl coupled with various tin-containing promoters, including tributyltin bromide, tributyltin chloride and trimethyltin chloride.

TABLE 1[a,b]

| | | Liquid Product Composition (wt. %)[c] | | | | | | EGMBE[d] |
|---|---|---|---|---|---|---|---|---|
| Example | Catalyst Composition | $H_2O$ | MeOH | BuOH | EGMBE | EGDBE | EG | Yield (Mole %) |
| 4 | $Co_2(CO)_8$—$Ph_3GeCl$ | 4.9 | 0.3 | 72.4 | 12.2 | 1.4 | 0.2 | 45 |
| 5 | $Co_2(CO)_8$—$Me_3GeBr$ | 5.1 | 0.3 | 73.8 | 11.3 | 1.5 | 0.2 | 42 |
| 6 | $Co_2(CO)_8$—$Et_3GeCl$ | 4.9 | 0.3 | 72.9 | 12.3 | 1.4 | 0.2 | 46 |
| 7 | $Co_2(CO)_8$—$Ph_4Ge$ | 4.5 | 0.4 | 74.2 | 14.0 | 1.0 | 0.5 | 53 |
| 8 | $Co_2(CO)_8$—$Et_4Ge$ | 5.1 | 0.3 | 70.9 | 13.2 | 1.6 | 0.3 | 50 |
| 9 | $Co_2(CO)_8$—$Ph_3GeH$ | 4.7 | 0.4 | 72.6 | 13.0 | 1.4 | 0.3 | 47 |

[a]Run Charge: Co, 2 mmoles; Co/Ge = 1/1; BuOH, 0.5 mole; HCHO, 0.1 mole.
[b]Run Conditions: 160° C., initial 2700 psig of $CO/H_2$ (1:2 molar), 4 hours.
[c]Designations: EGMBE, Ethylene glycol monobutyl ether; EGDBE, ethylene glycol dibutyl ether;
[d]EGMBE yield basis formaldehyde charged.

TABLE 2[a,b]

| | | Liquid Product Compositions (wt. %)[c] | | | | | | EGMBE[d] |
|---|---|---|---|---|---|---|---|---|
| Example | Catalyst Composition | $H_2O$ | MeOH | BuOH | EGMBE | EGDBE | EG | Yield (mole %) |
| 10 | $Co_2(CO)_8$—$Bu_3SnBr$ | 4.6 | 0.4 | 76.3 | 8.2 | 1.1 | 0.2 | 29 |
| 11 | $Co_2(CO)_8$—$Bu_3SnH$ | 1.7 | 0.9 | 93.0 | <0.1 | 0.3 | 0.4 | <2 |
| 12 | $Co_2(CO)_8$—$Bu_3SnOAc$ | 2.4 | 0.8 | 87.4 | 0.3 | 0.6 | 0.2 | <2 |
| 13 | $Co_2(CO)_8$—$Bu_3SnCl$ | 4.8 | 0.3 | 76.4 | 9.9 | 0.7 | 1.5 | 37 |
| 14 | $Co_2(CO)_8$—$Me_3SnCl$ | 4.6 | 0.3 | 73.1 | 8.8 | 0.9 | 0.2 | 33 |
| 15 | $Co_2(CO)_8$—$Ph_3SnCl$ | 3.8 | 0.6 | 85.2 | 0.9 | 0.3 | 0.3 | 3 |
| 16 | $Co_2(CO)_8$—$Ph_4Sn$ | 3.8 | 0.3 | 83.1 | 1.3 | 0.3 | 0.3 | 5 |
| 17 | $Co_2(CO)_8$—$SnCl_4$ | 4.4 | 0.4 | 82.4 | 1.4 | 0.8 | 0.2 | 5 |
| 18 | $Co_2(CO)_8$—$SnCl_2$ | 4.4 | 0.4 | 87.7 | 1.8 | 0.8 | 0.1 | 6 |

[a]Run Charge: Co, 2 mmoles; Co/Sn = 1/1; BuOH, 0.5 mole; HCHO, 0.1 mole.
[b]Run Conditions: 160° C.; initial 2700 psig of $CO/H_2$ (1:2 molar); 4 hours.
[c]Designations as per Table 1.
[d]EGMBE yield basis formaldehyde charged.

EXAMPLE 19

Following the procedure of Example 1, the reactor was charged with a mixture of dicobalt octacarbonyl (2 mmole Co), triphenylgermanium bromide (2 mmole) and paraformaldehyde (0.1 mole) in 16.0 g of methanol (0.5 mole). The mixture was flushed with $CO/H_2$, the reactor sealed, pressured to 2700 psig with $CO/H_2$ (1:2 molar) and heated with agitation to 180° C. After four hours, the reactor was allowed to cool, the excess gas vented and the liquid product (23.4 g) recovered.

Analysis of the liquid product showed it to contain 8.4 wt. % of ethylene glycol monomethyl ether and 0.7 wt. % of ethylene glycol dimethyl ether. Cobalt recovery in solution was >98% of that originally charged, there was no solid product phase.

EXAMPLE 20

Following the general procedure of Example 1, the 450 ml glass-lined pressure reactor was charged with 0.1 mole of paraformaldehyde, dicobalt octacarbonyl (2.0 mmole Co), triphenylgermanium bromide (2.0 mmole) and 0.5 mole of n-butanol. After flushing with syngas ($CO/H_2$ mixture), the reactor was pressured to 2700 psig with a gaseous mixture containing 2 moles of hydrogen per mole of carbon monoxide, and heated to 160° C. with agitation. After 4 hours at temperature, the reactor was cooled and vented and the clear red liquid product (44.5 g) recovered and analyzed by glc and Karl Fischer titration. There were no residual solids at this state.

The product liquid was distilled in vacuo, and ethylene glycol monobutyl ether was recovered as a distillate fraction at 48°-52° C. (1 mm Hg pressure). The residual catalyst remained behind as a deep-red colored liquid (3.6 g) and this residual catalyst liquid was returned to the 450 ml glass-lined reactor by washing with additional n-butanol (0.5 mole). Fresh paraformaldehyde (0.1 mole) was also added at this stage, the reactor sealed, flushed with syngas, pressured to 2700 psig with $CO/H_2$ (1:2 molar) and heated to 160° C. with agitation for 4 hours. In this manner the synthesis of ethylene glycol monobutyl ether was repeated successfully, and the later recovered from the crude liquid product (44.6 g) by vacuum distillation as outlined above.

The residual catalyst solution (5.1 g) from this second cycle was again returned to the reactor for further glycol ether synthesis. The yields of glycol monobutyl ether (basis paraformaldehyde charged) for this three cycle experiment are shown in Table 3.

TABLE 3

| Ethylene Glycol Butyl Ethers From Syngas-Catalyst Recycling | | |
|---|---|---|
| Example | Number of Catalyst Cycles | Yield of $BuOCH_2CH_2OH$ (%)[a] |
| 20 | 1 | 46 |
|  | 2 | 47 |
|  | 3 | 45 |

[a]Yield basis paraformaldehyde charged (0.1 mole) at the start of each catalyst cycle.

What is claimed is:

1. A process for preparing ethylene glycol monoalkyl ethers which comprises reacting hydrogen, carbon monoxide and a material selected from the group consisting of:

(a) formaldehyde and an alcohol of the formula:

ROH, wherein R is alkyl of from 1 to 10 carbon atoms, and (b) an acetal of the formula:

$(R'O)_2CH_2$ wherein R is alkyl of from 1 to 10 carbon atoms, in the presence of a catalyst comprising a cobalt-containing compound and a promoter selected from the group consisting of a tin-containing compound and a germanium-containing compound, at superatmospheric pressures of about 500 psig or greater and at a temperature of about 50° to about 300° C. until substantially formation of the said ethylene glycol monoalkyl ether has been achieved and recovering the said ether from the reaction mixture.

2. The process of claim 1 wherein the said reaction mixture is heated at a temperature of about 100° to about 250° C.

3. the process of claim 1 wherein the process is conducted at a pressure of about 1000 psig to about 5000 psig.

4. The process of claim 1 wherein the said cobalt-containing compound is selected from the group consisting of one or more oxides of cobalt, cobalt salts of a mineral acid, cobalt salts of an organic carboxylic acid and cobalt carbonyl or hydrocarbonyl derivatives.

5. The process of claim 1 wherein the said cobalt-containing compound is selected from the group consisting of cobalt oxide, cobalt chloride, cobalt iodide, cobalt nitrate, cobalt sulfate, cobalt acetate, cobalt propionate, cobalt acetylacetonate, and dicobalt octacarbonyl.

6. The process of claim 1 wherein said cobalt containing compound is dicobalt octacarbonyl.

7. The process of claim 1 wherein said material is formaldehyde and an alcohol of the formula:

ROH, wherein R is alkyl of from 1 to 10 carbon atoms.

8. The process of claim 7 wherein the said alcohol is n-butanol.

9. The process of claim 7 wherein the said alcohol is methanol.

10. The process of claim 7 wherein the said alcohol is ethanol.

11. The process of claim 1 wherein the said material is an acetal of the formula:

$(R'O)_2CH_2$, wherein R' is alkyl of from 1 to 10 carbon atoms.

12. The process of claim 11 wherein the reaction is conducted in the presence of an alcohol of the formula:

R"OH, wherein R" is alkyl of from 1 to 10 carbon atoms.

13. The process of claim 11 wherein the said acetal is dimethoxymethane.

14. The process of claim 11 wherein the said acetal is dibutoxymethane.

15. The process of claim 1 wherein the said promoter is a tin-containing compound.

16. The process of claim 15 wherein the said tin-containing compound is tributyltin bromide.

17. The process of claim 15 wherein the said promoter is tributyltin chloride.

18. The process of claim 15 wherein the said promoter is trimethyltin chloride.

19. The process of claim 1 wherein the said promoter is germanium-containing compound.

20. The process of claim 19 wherein the said germanium-containing compound is triphenylgermanium bromide.

21. The process of claim 19 wherein the said germanium-containing compound is selected from the group consisting of triphenylgermanium hydride, tetraphenylgermane, tetraethylgermane, triphenylgermanium chloride, trimethylgermanium bromide and triethylgermanium chloride.

22. The process of claim 1 wherein the said material is formaldehyde and n-butanol, the said cobalt-containing compound is dicobalt octacarbonyl and the said promoter is triphenylgermanium bromide.

23. The process of claim 1 wherein the said material is formaldehyde and n-butanol, the said cobalt-containing compound is dicobalt octacarbonyl and the said promoter is triphenylgermanium hydride.

24. The process of claim 1 wherein the said material is dibutoxymethane, the said cobalt-containing compound is dicobalt octacarbonyl and the said promoter is triphenylgermanium bromide.

* * * * *